United States Patent
Kühnle et al.

(10) Patent No.: US 10,940,037 B2
(45) Date of Patent: Mar. 9, 2021

(54) PRIMARY PACKAGING AND METHOD FOR THE MANUFACTURE OF A PRIMARY PACKAGING

(71) Applicant: VETTER PHARMA-FERTIGUNG GmbH & Co. KG, Ravensburg (DE)

(72) Inventors: Sarah Kühnle, Friedrichshafen (DE); Frank Böttger, Ravensburg (DE); Paul Nelles, Ravensburg (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 193 days.

(21) Appl. No.: 15/567,763

(22) PCT Filed: Apr. 21, 2016

(86) PCT No.: PCT/EP2016/058895
§ 371 (c)(1),
(2) Date: Oct. 19, 2017

(87) PCT Pub. No.: WO2016/170054
PCT Pub. Date: Oct. 27, 2016

(65) Prior Publication Data
US 2018/0133054 A1    May 17, 2018

(30) Foreign Application Priority Data
Apr. 21, 2015    (DE) .................... 10 2015 207 228.2

(51) Int. Cl.
*A61F 9/00*    (2006.01)
*A61M 5/31*    (2006.01)
*A61M 5/19*    (2006.01)

(52) U.S. Cl.
CPC ............. *A61F 9/0008* (2013.01); *A61M 5/19* (2013.01); *A61M 5/3129* (2013.01); *A61M 2005/3131* (2013.01); *A61M 2205/0238* (2013.01)

(58) Field of Classification Search
CPC ..... A61F 9/0008; A61M 5/19; A61M 5/3129; A61M 2005/3131; A61M 2205/0238
See application file for complete search history.

(56) References Cited

U.S. PATENT DOCUMENTS 5,654,054 A    8/1997  Tropsha et al.
5,817,082 A *  10/1998 Niedospial, Jr. ...... A61J 1/2096
                                                 604/414
(Continued)

FOREIGN PATENT DOCUMENTS

DE    4438360 A1   5/1996
DE    69314458 T2  4/1998
(Continued)

OTHER PUBLICATIONS

International Search Report for PCT/EP2016/058895, ISA/EP, Rijswijk, NL, dated Jul. 11, 2016.
(Continued)

*Primary Examiner* — Theodore J Stigell
(74) *Attorney, Agent, or Firm* — Stephen T. Olson; Harness, Dickey & Pierce, P.L.C.

(57) ABSTRACT

A primary packaging for medical preparations includes a base body having a plastic material. The base body has at least one wall including an outer surface and at least one inner surface. The outer surface of the primary packaging is provided with a gas tight coating.

14 Claims, 1 Drawing Sheet

(56) References Cited

U.S. PATENT DOCUMENTS

| | | | |
|---|---|---|---|
| 6,331,174 B1 | 12/2001 | Reinhard et al. | |
| 6,450,994 B1* | 9/2002 | Boyles | A61F 9/0008 222/420 |
| 2001/0004466 A1 | 6/2001 | Heinz et al. | |
| 2005/0192530 A1 | 9/2005 | Castellano | |
| 2008/0241521 A1 | 10/2008 | Solovyov et al. | |
| 2009/0220717 A1 | 9/2009 | Wilczak et al. | |
| 2011/0186537 A1* | 8/2011 | Rodriguez San Juan | A61M 5/3129 215/355 |
| 2012/0175384 A1* | 7/2012 | Greter | A61M 5/19 222/137 |
| 2013/0041241 A1* | 2/2013 | Felts | C23C 16/045 600/364 |
| 2014/0249484 A1* | 9/2014 | Jones | A61M 5/31513 604/230 |
| 2015/0132312 A1* | 5/2015 | McAlvin | A61M 1/3679 424/140.1 |
| 2015/0224263 A1* | 8/2015 | Dugand | B29C 45/14622 604/218 |
| 2015/0290077 A1 | 10/2015 | Sano et al. | |
| 2015/0374938 A1* | 12/2015 | Scheiber | A61M 15/06 128/203.21 |
| 2016/0015600 A1* | 1/2016 | Weikart | A61L 31/04 206/461 |

FOREIGN PATENT DOCUMENTS

| | | |
|---|---|---|
| EP | 0511402 A1 | 11/1992 |
| EP | 0920879 A2 | 6/1999 |
| JP | H04246364 A | 9/1992 |
| JP | H10201844 A | 8/1998 |
| JP | 2004057819 A | 2/2004 |
| JP | 2008/0245822 A | 10/2008 |
| JP | 2014533177 A | 12/2014 |
| WO | WO-2014/065359 A1 | 5/2014 |

OTHER PUBLICATIONS

Written Opinion of the ISA for PCT/EP2016/058895, ISA/EP, Rijswijk, NL, dated Jul. 11, 2016.

Russian Office Action in parallel application 2017/140258/15(069940), FIPS, Moscow, dated Sep. 12, 2018., with English translation attached.

Ref D2: V.I. Chueshov et al, Technology of Medicines of Industrial Manufacture// Textbook.—Vinnitsa: Nova Kniga, 2014.—Part 1, p. 107-108, with English translation attached.

Japanese Office Action in parallel application 22017-554830, dated Mar. 19, 2019., with English translation attached.

International Preliminary Report on Patentability regarding International Application No. PCT/EP2016/058895, dated Oct. 24, 2017.

Office Action regarding Japanese Patent Application No. 2017-554830, dated Aug. 27, 2019.

Office Action regarding Japanese Patent Application No. 2017-554830, dated Jan. 7, 2020.

* cited by examiner

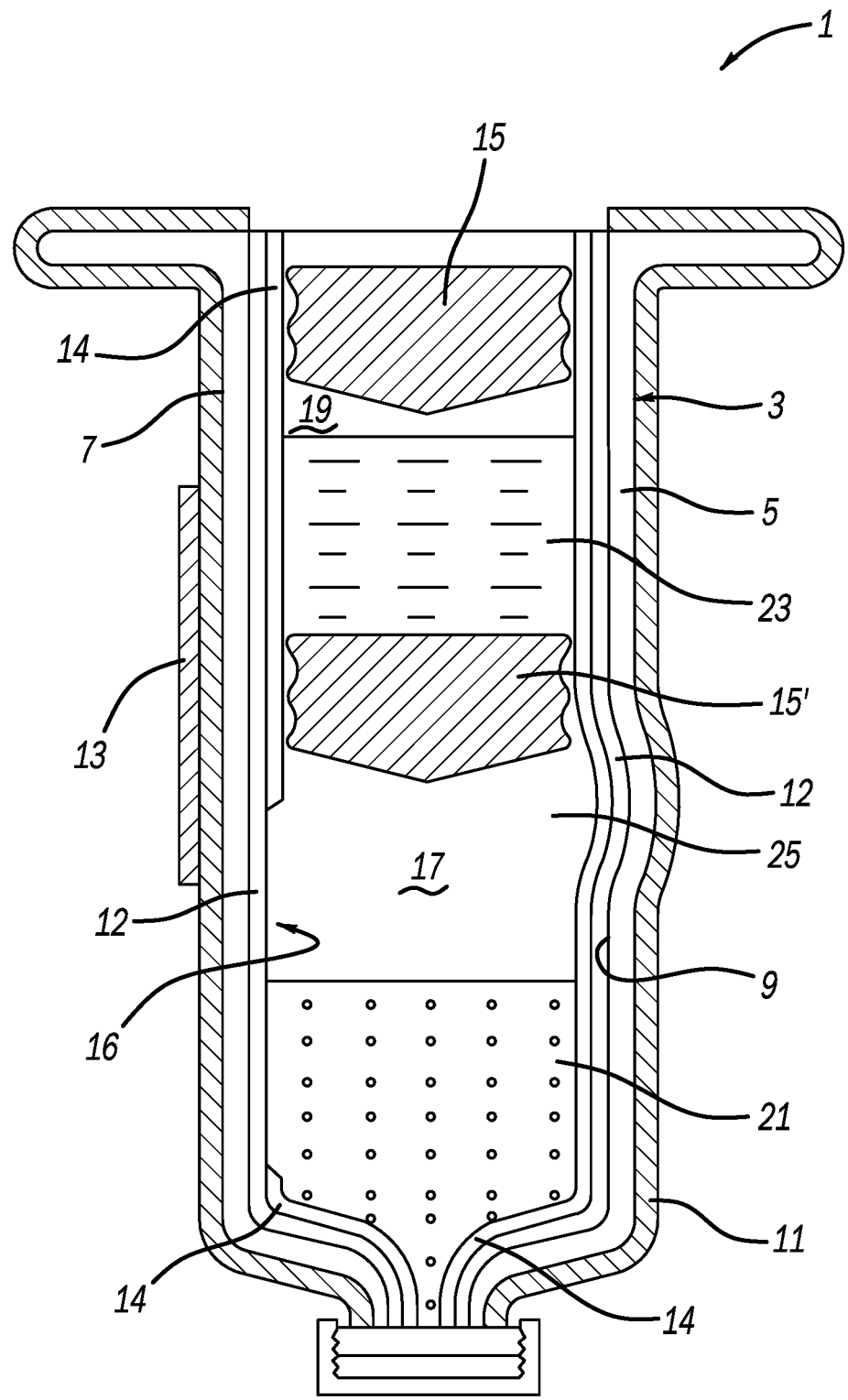

PRIMARY PACKAGING AND METHOD FOR THE MANUFACTURE OF A PRIMARY PACKAGING

CROSS-REFERENCE TO RELATED APPLICATIONS

This application is a 371 U.S. National Stage of International Application No. PCT/EP2016/058895, filed Apr. 21, 2016, which claims the benefit of and priority to German Patent Application No. 10 2015 207 228.2, filed Apr. 21, 2015. The entire disclosures of the above applications are incorporated herein by reference.

DESCRIPTION

The present invention relates to a primary packaging for medical preparations and a method for the manufacture of such a primary packaging.

Primary packagings, in particular prefilled syringes or dual chamber systems, are used for storing and parenterally administering active ingredients and/or auxiliary agents. For this purpose, there are applications which, in addition to an inner sterility of the primary packaging required anyway, also require an outer sterility, thus, in particular require a sterility of the outer surface of the primary packaging. In particular, this relates to primary packagings for ophthalmic preparations for the purpose of injections, which in recent years have gained increased importance by the approval of new, modern drugs for treating macular degeneration. Such primary packagings have to be subjected to treatment in a secondary packaging, for example a blister pack, which ensures the outer sterility. In this instance, thermal or radiation-intensive methods are eliminated, because otherwise the active substance in the primary packaging would be damaged. For this reason, typically chemical sterilizations, for example a treatment using ethylene oxide or using vaporized hydrogen peroxide, are selected. In this instance, the primary packaging has to be sufficiently sealed against the ingress of such reagents to prevent a contamination of the content. This generally makes it more difficult to choose the materials for the primary packaging. Primary packagings made from glass fulfill the mentioned requirements; however, they result in a very high development and control effort, in particular, to achieve a still tolerable quantity of subvisual particles in a solution to be injected. This is in particular the case if such glass bodies in their interior are siliconized for improving the sliding properties of a plug. In addition, there is the risk which emanates from detaching, microscopic glass particles resulting during storage or transport, but which cannot be seen with the naked eye. The specific disadvantages of primary packaging made from glass can be bypassed by primary packaging made from plastic; however, highly transparent plastics typically used for this purpose have the disadvantage to be permeable to gas.

The object of the present invention is to create a primary packaging and a method for the manufacture of such a primary packaging, in which the mentioned disadvantages do not occur.

This object is achieved by the provisions of the independent claims. Advantageous embodiments result from the dependent claims.

The object is in particular achieved in that a primary packaging for medical preparation is created, having a base body which features a plastic material or is formed from a plastic material, the base body having at least one wall including an outer surface and at least one inner surface. For this purpose, the outer surface is facing the outside of the primary packaging, the inner surface facing an interior of the primary packaging, in particular an interior for accommodating an active substance and/or auxiliary agent or a solvent. It is in particular possible that the primary packaging has a cylindrical wall, which has an outer surface shell and an inner peripheral surface. The primary packaging is characterized by the fact that the outer surface is provided with a gas tight coating. The primary packaging has advantages vis-a-vis the state of the art. In particular, the advantages, which generally are connected to a base body formed from plastic material compared to a primary packaging made from glass, as a significantly lower quantity, if any, of subvisual particles in solvents can namely be expected, are realized so that also the development and control effort associated with the primary packaging is significantly lower. Furthermore, there is no risk of detaching, microscopic glass particles. The gas tight coating provided at the outer surface lends the primary packaging impermeable properties, in particular to reagents used for a chemical sterilization. For this purpose, an outer sterility is able to be ensured for the primary packaging by chemical sterilization, for example, using ethylene oxide or vaporized hydrogen peroxide. In so doing, the primary packaging is sufficiently sealed against an ingress of these reagents on account of the gas tight coating of the outer surface.

Preferably, the outer surface of the base body in its entirety is, in particular, seamlessly provided with a gas tight coating. As a result, it is eliminated that, during a terminal sterilization, residues of the sterilization means may diffuse via potential unprotected plastic regions into the interior of the primary packaging.

Preferably, the gas tight coating is provided as an immobilized layer at the outer surface. This immobilized layer is thus situated at the outer surface in a longterm-stable and unmodifiable manner as well as in a fixed and secured manner.

Particularly preferably, the gas tight coating has properties impermeable to oxygen, carbon dioxide, ethylene oxide, and/or hydrogen peroxide. In this instance, these are particularly common reagents, which are used for chemical terminal sterilization to ensure the outer sterility of the primary packaging.

Preferable is an exemplary embodiment of the primary packaging which is characterized by the fact that the gas tight coating has a layer which features a metal or metalloid or which is made up of a metal or metalloid. Preferably, the layer has in particular a metal or metalloid film or is made up of a metal or a metalloid film. For this purpose, the layer may include in particular gold, aluminum, chromium, silver or another suitable metal or metalloid, or may be made up of one of the mentioned metals or another suitable metal or metalloid.

Alternatively or additionally, it is possible that the gas tight coating has a layer which has a silicon or a silicon compound-preferably including a quartz-like or vitreous composition-or is made up of silicon or a silicon compound-preferably including a quartz-like or vitreous composition. Particularly preferably, the layer has a film built-up of a silicon compound including a vitreous composition or is made up of such a film. This includes in particular quartz-like coatings.

Such a layer made of metal or a metalloid, or else from silicon or a silicon compound—in particular having a vitreous composition-provides the desired gas barrier properties. In this instance, the gas tight coating may have in particular a plurality of similar or different sublayers, in particular being negligibly different in their composition, or may be made up of such sublayers.

It is also possible that the gas tight coating features diamond or is made up of diamond. Alternatively or additionally, It is also possible that the gas tight coating features Teflon or is made up of Teflon.

Preferable is also an exemplary embodiment of the primary packaging which is characterized by the fact that the base body features a transparent plastic material or is made up of a transparent plastic material. The transparent plastic material is preferably selected from a group made up of a cyclic olefin polymer (COP), a cyclic olefin copolymer and polycarbonate (PC). The materials are suited, in particular, for the manufacture of transparent base bodies for a primary packaging.

Preferable is also an exemplary embodiment of the primary packaging which is characterized by the fact that an adhesive agent layer is situated between the outer surface and the gas tight coating. For this purpose, the adhesive agent layer serves an improved adhesion of the gas tight coating on the outer layer. In particular, the adhesive agent layer preferably enables a covalent bonding of the gas tight coating built-up on the adhesive agent layer.

Preferable is also an exemplary embodiment of the primary packaging which is characterized by the fact that a functional layer is situated at least in sections or also completely on the gas tight coating. In this instance, the functional layer serves to provide a specific function or, in particular, serves a local improvement of the properties of an outer surface of the gas tight coating for a specific function. For this purpose, the functional layer may be provided, for example, to provide a better adhesion for adhesive labels. In particular, this may concern an immobilized layer, which has properties that inhibit that substances of outer markings or labels, in particular adhesive labels, can migrate into the packaged product. The functional layer may also be provided to apply dyes or markings, the functional layer in this instance having in particular better properties than the gas tight coating itself. Additionally or alternatively, a functional layer may be provided which, compared to the gas tight coating, has a reduced susceptibility to scratches or cosmetic defects.

It is possible that the primary packaging has a plurality of functional layers, which may be configured and provided for different purposes, and different functional layers may be provided in particular locally at different locations of the primary packaging. It is also possible that different functional layers are situated one above the other, and, in this way, they are able to ensure different functions cumulatively in one location of the primary packaging.

Preferably, the at least one functional layer is formed as an immobilized layer and, in this way, is situated in a particularly stable, fixed and secure manner on the gas tight coating. It is possible that the gas tight coating and also the at least one functional layer include a silicon or a silicon compound, in particular, including a quartz-like or vitreous composition. For this purpose, it is possible that the gas tight coating and the at least one functional layer differ in oxygen content. In particular, these two layers may be quartz-like layers, but having different oxygen contents.

It is in particular possible that the oxygen content of the at least one functional layer is higher than the oxygen content of the gas tight coating. The higher the oxygen content of the quartz-like coating, the more vitreous is the coating. In this instance, it becomes evident that, for example, adhesive labels are optimized for an adhesive bonding with glass. For this reason it is advantageous, at least in an area in which an adhesive label is to be affixed, to provide a preferably vitreous functional layer on the gas tight coating, for example, in that the oxygen content of the coating is there, in particularly locally, increased.

Also preferable is an exemplary embodiment of the primary packaging which is characterized by the fact that the inner surface is provided with a gas tight inner coating. In so doing, the gas tightness of the primary packaging is additionally increased, because the gas tight coating of the outer surface and the gas tight inner coating together provide a particularly high tightness in relation to gaseous substances, in particular to substances for chemical sterilization. Preferably, the gas tight inner coating is provided as an immobilized layer at the outer surface.

Particularly preferably, the gas tight inner coating has at least one of the properties which previously have been described for the coating of the outer surface. In particular, the inner coating preferably has at least one layer, which features a metal or metalloid or is made up of a metal or metalloid, or which has a silicon or a silicon compound—preferably including a quartz-like or vitreous composition—or is made up of a silicon or a silicon compound—preferably including a quartz-like or vitreous composition. Furthermore, an adhesive agent layer is situated between the inner surface and the gas tight inner coating.

In particular metal or metalloid films, for example made of gold, aluminum, silver, chromium, or other suitable material, and/or films built-up of silicon or a silicon compound, particularly having a vitreous or quartz-like composition, can be considered for the gas tight inner coating. It is also possible that the gas tight inner coating is made out of a plurality of similar or, in particular in regard to the chemical composition, slightly different sublayers.

It is also possible that the gas tight inner coating features diamond or is made up of diamond. Alternatively or additionally, It is also possible that the gas tight inner coating features Teflon or is made up of Teflon.

Preferably, the inner surface of the wall of the base body is also completely and, in particular, seamlessly provided with the gas tight inner coating. It is however also possible to omit the gas tight inner coating locally or in sections.

Also preferable is an exemplary embodiment of the primary packaging, which is characterized by the fact that an inner functional layer is situated at least in sections on the gas tight coating. In this instance, this is preferably an immobilized layer. It namely has become evident that a packaged active substance and/or auxiliary agent in the packaged state has to be free of particulate contaminants during packaging and during storage. In particular for ophthalmic preparations, even the smallest particles in the visual region risk to permanently compromise the eyesight of the patient. The inner functional layer in total may be provided on the gas tight inner coating, but also only in sections or locally.

Moreover, the danger exists that a wall material of the primary packaging being in contact with an active substance and/or auxiliary agent decomposes during an aseptic freeze-drying, as a result of which particulate contaminants may again enter into the active substance and/or auxiliary agent. These risks and/or disadvantages may in particular be prevented using an immobilized inner functional layer, which is robust against decomposition and abrasion.

Additionally or alternatively, an inner functional layer is preferably provided, which reduces a sticking friction of elastomer materials, as a result of which it in particular enables a simplified dosing of small volumes. Moreover, a siliconization of the inner surface is not necessary, so that particulate contaminants hereby introduced are prevented.

Particularly preferably, the inner functional layer is configured in such a manner that it does not give off measurable particles or extraneous materials, for example silicon droplets, to the active substance and/or auxiliary agent.

Particularly preferably, the at least one inner functional layer is configured as an, in particular, impermeable lubricating film.

Preferably, the gas tight inner coating and/or the inner functional layer is/are omitted in sections, in particular locally. This means that in at least one preferably annularly circumferential free region of the inner surface no gas tight inner coating and/or no inner functional layer is/are situated. Thus, the free region is free of the gas tight inner coating and/or the inner functional layer. As a free region, the primary packaging has a region in which, when filling and freeze-drying the primary packaging according to specifications, a lyophilisate is disposed. Such a configuration is particularly preferable for a primary packaging configured as a dual chamber system, which is preferably devised for an ophthalmic application. In a dual chamber system, the free region is preferably an annular region distally above a center plug region, in which a center plug is situated according to specifications.

Particularly preferable is an exemplary embodiment, in which the inner surface of the wall of the base body is completely and, in particular, seamlessly provided with the gas tight inner coating, the inner functional layer being omitted in at least one free region.

It is after all furthermore possible to omit the inner-lying coating—in particular a lubricating layer—in a subregion. This is in particular advantageous for the region, in which a freeze-drying product solution comes into contact with the container wall and, if applicable, with the coating. In so doing, it generally can be prevented that interactions occur between product and coating during the manufacturing process, in particular during the freeze-drying, of the medication and when storing the medication, which negatively affects the product quality. For ophthalmic products, undesirable interactions could, for example, result in silicon droplets in solutions or in the occurrence of coating fragments.

Additionally or alternatively, an inner functional layer is provided, which has—as required for a specific primary packaging—hydrophobe or hydrophilic properties. A hydrophobe layer has preferably a polydimethylsiloxane or a perfluorinated compound, such as polytetrafluoroethylene (PTFE), or it is made up of one of the mentioned substances. The hydrophobe layer preferably has in particular a film, which features one of the mentioned substances or is made up of one of the mentioned substances. A hydrophilic inner functional layer preferably features carboxyl groups, and such a hydrophilic inner functional layer can be manufactured in particular by plasma-induced polymerization of acrylic acid.

In general, such hydrophobe or hydrophilic inner functional layers serve to reduce sticking friction and, in particular, the full drainability, and a hydrophobe inner functional layer being provided for the full drainability of an aqueous active substance and/or auxiliary agent, and a hydrophilic inner functional layer being provided for the full drainability of a hydrophilic active substance and/or auxiliary agent.

The at least one functional layer preferably has a crosslinkability or crosslink, in particular in the form of additional functional groups, reactive groups, radical groups, ionic groups, double bonds or other functional groups, which can be linked to one another, in particular by UV irradiation of the inner functional layer. In so doing, the molar mass of the inner functional layer can be increased, as as a result of which the inner functional layer can be in particular configured in an immobile manner, so that a detachment or a migration of the inner functional layer into the active substance and/or auxiliary agent can be prevented.

Particularly preferable is an exemplary embodiment of the primary packaging which is characterized by the fact that the primary packaging is configured as a dual chamber system. For this purpose, the dual chamber system may be configured, in particular, as a dual chamber cartridge or a dual chamber syringe, the dual chamber system having a first chamber for a medical preparation in hydrophilic, powdered or liquid form. In a second chamber, a liquid form is present, in particular a solvent, which immediately prior to administering serves to dissolve the solid medical preparation in the first chamber, or serves the intermixture with a liquid medical preparation present in the first chamber close to the time of an injection.

Alternatively, it is possible that the primary packaging is configured as a single chamber cartridge or as a single chamber syringe.

Particularly preferable is an exemplary embodiment of the primary packaging, which is configured for an ophthalmic application. In this instance, the primary packaging is in particular characterized by a small filling volume of, as a rule, less than or at most 200 µl. This is owing to the fact that typically no more than 50 µl are to be injected into the vitreous body of the human eye. Preferably, exterior labels are disposed at the primary packaging to enable a simplified dosing for the physician. A suitably dimensioned format for the primary packaging is a volume of 1 ml or 0.5 ml. Ophthalmic preparations for the purpose of injections have in recent years gained increased importance by the approval of new, modern drugs for the treatment of macular degeneration. Hence, the primary packaging has preferably a preparation for the treatment of macular degeneration, in particular, the treatment of age-related macular degeneration, diabetes-induced macular degeneration, wet AMD or another macular degeneration.

Particularly preferably, the primary packaging is configured as a dual chamber cartridge or a dual chamber syringe for the ophthalmic application. Alternatively, it is possible that the primary packaging is configured as a single chamber cartridge or a single chamber syringe for the ophthalmic application.

The primary packaging is preferably delivered in presterilized form and/or in a tray or tub.

The object of the present invention is in particular also achieved in that a method for the manufacture of a primary packaging is created, including the following steps: a base body formed from plastic material is provided for the primary packaging, and an outer surface of a wall of the base body is coated by a gas tight coating. Particularly preferably, a primary packaging is, within the scope of the method, manufactured according to one of the previously described exemplary embodiments. Within the scope of the method, in particular those advantages are realized, which have been described in connection with the primary packaging. In so doing, the primary packaging manufactured with the aid of the method does, in particular, not have the disadvantages of a primary packaging made of glass, the primary packaging at the same time being gas tight, in particular vis-à-vis the substances used for the chemical sterilization, for example, ethylene oxide, oxygen, carbon dioxide, or hydrogen peroxide.

Preferably, the complete surface of the base body, in particular an outer surface of the base body in its entirety, is seamlessly provided with the gas tight coating. During a later terminal sterilization, residues of a sterilizing agent may not diffuse into an active substance and/or auxiliary agent disposed in the primary packaging via potential unprotected areas of the outer surface.

It is possible that the gas tight coating is produced in one single coating cycle. Also preferred is however an embodiment of the method in which the gas tight coating is produced in a plurality of coating cycles, and in particular a plurality of similar or different sublayers, in particular sublayers negligibly different in their composition in regard to its chemical composition, can be generated. In this instant, it is in particular possible to vary the properties of the gas tight coating, emanating from the outer surface, in a flexible manner and according to demand and, in this way, to build up along its height—in relation to the primary packaging, thus, in the radial direction—an unalterable layer having variable properties.

Particularly preferable is an exemplary embodiment, in which the gas tight coating features silicon or a silicon compound, an oxygen content of the in particular quartz-like or vitreous coating being varied along a height of the layer or in the radial extension of the primary packaging, and the oxygen fraction increasing outwardly, preferably starting from the outer surface of the wall of the base body. As a result, a good adhesion of the gas tight coating on the outer surface of the base body made of plastic material is ensured, the quartz-like or vitreous properties of the gas tight coating increasing in the outward direction. Thus, the gas tight coating in the outward direction becomes more scratch resistant, more immobile and more suitable to provide a good adhesion for adhesive labels, dyes or markings.

An exemplary embodiment of the method is preferred, which is characterized by the fact that the base body has been pretreated. In this instance, the plastic material of the base body is preferably functionalized at the outer surface, in particular to enable a covalent bonding of the gas tight coating building-up on the plastic material of the base body. Hence, an adhesive promoter between the outer surface and the gas tight coating is realized. In a preferred embodiment of the method, the base body is pretreated by a plasma treatment and/or by a wet chemical method. In so doing, functional groups, in particular radical, ionic and/or highly polar groups, result at the outer surface, which enable a good adhesive bonding to the gas tight coating.

Also preferred is an embodiment of the method, which is characterized by the fact that an inner surface of the wall of the base body is coated by a gas tight inner coating. This inner coating is preferably produced in one coating cycle or in a plurality of coating cycles, as it has been already explained in connection with the gas tight coating of the outer surface. Particularly preferably, the inner coating is produced in relation to at least one method step, so as it has been explained previously for the outer coating.

In particular, it is preferably provided that a surface of the inner surface in its entirety is seamlessly provided with the gas tight inner coating. This serves-just as explained for the outer surface—an improved gas tightness of the primary packaging. It is however also possible to omit the gas tight inner coating locally or in sections.

Also preferred is an embodiment of the method, in which the gas tight coating on the outside and/or the gas tight inner coating on the inside is provided at least in sections or completely with at least one functional layer, which in connection with the inner coating is also referred to as inner functional layer. To simplify the illustration, in the following in part reference is generally made to a "functional layer", the inner functional layer being included in this reference. The at least one functional layer is preferably configured as an immobilized layer. As an inner functional layer, the functional layer is preferably configured to reduce a sticking friction of elastomer plugs, to generally provide a decreased susceptibility to scratches or cosmetic defects, to ensure an improved adhesion of adhesive labels, dyes and/or markings, and/or to prevent that substances of outer markings or labels can migrate in the interior of the base body into the active substance and/or auxiliary agent. The functional layer preferably has hydrophobe or hydrophilic properties. In particular, it is possible that the functional layer is formed from at least one film, which includes polydimethylsiloxane or a perfluorinated compound, for example PTFE, or is made up of one of the mentioned substances.

Preferably, the gas tight inner coating and/or the inner functional layer is/are omitted in sections, in particular locally. This means that in at least one preferably annularly circumferential free region of the inner surface no gas tight inner coating and/or no inner functional layer is/are situated. In particular in a dual chamber system, a region is preferred as a free region, in which, when filling and freeze-drying the primary packaging according to specifications, a lyophilisate is disposed, in particular an annular region distally above a center plug region, in which a center plug is situated according to specifications, is omitted or kept free of the gas tight coating and/or the inner functional layer.

Particularly preferable is an embodiment of the method, in which the inner surface of the wall of the base body is completely and, in particular, seamlessly provided with the gas tight inner coating, the inner functional layer being omitted in at least one free region.

It is also possible that the adhesive agent layer, the gas tight coating or inner coating and/or the at least one functional layer merge one with another, preferably each of these layers featuring silicon, in particular having a quartz-like or vitreous composition, and an oxygen content preferably being varied along the sequence of the layers. In this way, preferably the adhesive agent layer is produced using a lower oxygen content, the gas tight coating is produced using a medium oxygen content and the at least one functional layer is produced using a higher oxygen content.

The gas tight coating and/or the gas tight inner coating may also be formed from thin metal or metalloid films, for example gold, silver aluminum, chromium or another suitable metal. The gas tight coating and/or the gas tight inner coating can also be formed from diamond or from Teflon.

Preferred is an embodiment of the method, which is characterized by the fact that a layer including silicon or a silicon compound is, viewed in the radial direction, generated having a variable oxygen fraction. This layer may be built-up on the outer surface and/or on the inner surface. In this instance, the properties of the layer vary, in particular ranging from properties promoting adhesion to properties which are particularly scratch and defect resistant and/or are suitable for affixing labels, as this has been already explained previously.

Preferably, the gas tight coating and/or the gas tight inner coating is/are produced by chemical vapor deposition (CVD), particularly preferably by plasma enhanced chemical vapor deposition (PECVD). Alternatively or additionally, it is however also possible that the gas tight inner coating and/or the gas tight coating is/are produced by physical vapor deposition (PVD) or by sputtering.

As a starting material for the gas tight coating and/or the gas tight inner coating, preferably a silicon containing substance is used, particularly preferably hexamethyldisiloxane (HMDSO). The silicon containing substance, preferably hexamethyldisiloxane (HMDSO), is preferably applied with the aid of plasma enhanced chemical vapor deposition (PECVD). In so doing, oxygen is preferably admixed to the hexamethyldisiloxane, the oxygen fraction being increased during the course of the coating, so that a vitreous or quartz-like coating is gradually formed. For this purpose, the oxygen fraction can be increased in the form of a continuous gradient or also in a step-growth manner.

It is also possible to use a metal or metalloid, for example gold silver, aluminum, chromium or another suitable material, as a starting material for the gas tight coating and/or the gas tight inner coating. In this instance, in particular semi-transparent layers and/or reflective layers may be generated as a function of the layer thickness.

Finally, preferred is an embodiment of the method, in which at least one layer selected from the gas tight coating and the gas tight inner coating is crosslinked. In this instance, functional groups, reactive groups, radical groups, ionic groups, double bonds or other functional groups, which react with one another and, in this way, are able to form a three-dimensional network within the layer, are provided in particular by a plasma treatment. It is possible that the linking is activated with the aid of UV irradiation. In so doing, the molar mass of the layer may be increased and the layer can be very effectively immobilized.

Preferably, the gas tight inner coating and the gas tight coating are applied to the outer surface in one single method step.

The description of the primary packaging on the one hand and of the method on the other hand are to be understood as being complementary to each other. Features of the primary packaging, which are explicitly or implicitly explained in connection to the method, are preferably, individually or combined with each other, features of a preferred exemplary embodiment of the primary packaging. Method steps which have been explicitly or implicitly explained in connection to the primary packaging, are preferably, individually or combined with each other, steps of a preferred embodiment of the method. Preferably, this embodiment is characterized by at least one method step, which results from at least one feature of the primary packaging. The primary packaging is preferably characterized by at least one feature which results from at least one step of a preferred embodiment of the method.

The present invention is subsequently explained in greater detail on the basis of of the drawing. In this instance, the single FIGURE shows a schematic illustration of an exemplary embodiment of a primary packaging.

The single FIGURE shows a schematic illustration of an exemplary embodiment of a primary packaging 1 for medical preparations, which has a base body 3 formed from plastic material, base body 3 preferably being made of plastic material. The base body has a wall 5, which has an outer surface 7 and an inner surface 9. For such primary packaging 1 made from plastic material, generally the problem exists that reagents used for ensuring an outer sterility in a chemical sterilization may enter through the plastic material of base body 3 into the interior of primary packaging 1 and can contaminate active substances and/or auxiliary agents present in the interior.

In order to prevent this from occurring, outer surface 7 here is provided with a gas tight coating 11. For this purpose, it is particularly provided that complete outer surface 7 is seamlessly provided with gas tight coating 11, so that, during a terminal sterilization of prefilled primary packaging 1, no sterilizing agent residues may diffuse via possible unprotected areas of base body 3 into active substances and/or auxiliary agents present in primary packaging 1.

Preferably, the gas tight coating is applied with the aid of chemical vapor deposition (CVD), in particular with the aid of plasma enhanced chemical vapor deposition (PECVD), physical vapor deposition (PVD) or sputtering.

Preferably, before applying gas tight coating 11, an adhesive agent layer not shown in the FIGURE is applied to outer surface 7.

Preferably, gas tight coating 11 features a metal or metalloid, the gas tight coating particularly preferably being made up of at least one metal or metalloid. In particular gold, silver, aluminum, chromium or other suitable materials can be considered as metal or metalloid materials. Alternatively or additionally, gas tight coating 11 preferably features silicon or a silicon compound-preferably including a quartz-like or vitreous composition—or is made up of silicon or a silicon compound—preferably including a quartz-like or vitreous composition. It is also possible that gas tight coating 11 features diamond or is made up of diamond. Alternatively or additionally, it is also possible that gas tight coating 11 features Teflon or is made up of Teflon.

The gas tight coating and the adhesive agent layer may also be produced in one single coating process and from the same starting material, preferably, in that a chemical composition of gas tight coating 11 is varied during the coating process.

Gas tight coating 11 is preferably formed from hexamethyldisiloxane (HMDSO), which is in particular applied by plasma coating using argon as a substrate gas by admixing oxygen. In so doing, in particular an oxygen fraction may be varied during the coating process, and the oxygen fraction can in particular be increased continuously or in steps. Hence, it is possible to first apply a layer quasi as an adhesive agent layer to outer surface 7, which features silicon having a lower oxygen fraction, the oxygen fraction then being outwardly increased so that gas tight coating 11 in the outward direction gains quartz-like or vitreous properties.

Base body 3 has preferably a cyclic olefin polymer (COP), a cyclic olefin copolymer (COC) or a polycarbonate (PC), or it is made up of one of the mentioned materials.

The FIGURE also shows that a functional layer 13 is situated at least in sections on gas tight coating 11. This functional layer is particularly configured to most advantageously provide adhesive properties for the adhesive labels. Alternatively or additionally, it is possible that functional layer 13 has a lower susceptibility to scratches or cosmetic defects than gas tight coating 11. For this purpose, functional layer 13 may also be integrally formed with gas tight coating 11, in particular, in that the oxygen fraction of a coating featuring silicon is even further increased. Thus, functional layer 13 particularly preferably is a quartz-like or vitreous layer, which has a higher oxygen fraction than gas tight coating 11.

Gas tight coating 11 and/or functional layer 13 is/are preferably immobilized, and a crosslink within at least one of these layers can in particular be provided.

Base body 3 preferably also has a gas tight inner coating 12, on inner surface 9. In this instance, it is here also possible that an adhesive agent layer is situated between inner surface 9 and the gas tight inner coating 12. Furthermore, it is possible that an inner functional layer 14 is at least in sections situated on the gas tight inner coating 12. This functional layer 14 is then in particular configured to reduce a sticking friction of elastomer plugs 15, 15' and, in this way, to in particular enable a simplified dosing even of smaller volumes. Furthermore, the gas tight inner coating 12 is preferably immobilized, so that it in particular does not give off any measurable particles or foreign substances, for example silicon droplets, to the active substances and/or auxiliary agents situated in primary packaging 1. Furthermore, the gas tight inner coating 12 and/or the at least one inner functional layer 14 feature(s) on the gas tight inner coating 12 preferably hydrophobe or hydrophilic properties. In this instance, these properties serve in particular to completely empty primary packaging 1, these properties preferably being adapted to the active substances and/or auxiliary agents disposed in primary packaging 1. A hydrophobe layer is preferably built up from at least one film, which is based on polydimethylsiloxane or a perfluorinated compound, for example, polytetrafluoroethylene (PTFE). A hydrophilic layer may, for example, be produced by plasma-induced polymerization of acrylic acid. In this instance, carboxyl groups result at the surface of the layer.

Furthermore, the gas tight inner coating 12 and/or the inner functional layer 14 applied on the inner coating 12 protect(s) primary packaging 1 preferably from decomposing during a freeze-drying process, so that in this instance particles cannot enter the active substances and/auxiliary agents disposed in primary packaging 1.

The gas tight inner coating 12 and/or the inner functional layer 14 may also be omitted in a free region 16, in particular to prevent an interaction with a freeze-drying material or a lyophilisate. In particular, only the inner functional layer 14 may be omitted in the free region 16.

Preferably, the layers lying on the inside and the layers built-up at outer surface 7 together are applied in one single method step.

The exemplary embodiment of primary packaging 1 shown in the FIGURE is configured as dual chamber system. In this instance, the dual chamber system has a first, distal chamber 17 and a second, proximal chamber 19. In first distal chamber 17, a first active substance and/or auxiliary agent 21 is disposed, in particular a lyophilized or pulverized active substance and/or auxiliary agent. In second proximal chamber 19, a second active substance and/or auxiliary agent 23 is disposed, in particular a liquid solvent. The separation of first active substance and/or auxiliary agent 21 and second active substance and/or auxiliary agent 23 serves in particular the extended storability of the medical preparation.

In a manner known per se, first distal chamber 17 and second proximal chamber 19 are connected to each other by a bypass 25. A first elastomer plug 15 serves as a terminal plug for carrying out an injection, a second elastomer plug 15' being situated as a center plug in a storage state of primary packaging 1 in such a manner in the area of bypass 25 that the bypass is blocked, as a result of which first chamber 17 is separated from second chamber 19. In order to condition primary packaging 1, first elastomer plug 15 in the FIGURE is downwardly displaced in the axial direction, as a result of which the pressure in second proximal chamber 19 is increased so that second elastomer plug 15' also moves in the distal direction. In so doing, finally bypass 25 is opened, so that second active substance and/or auxiliary agent 23, in particular the solvent, may flow from second chamber 19 into first chamber 17, where it mixes with first active substance and/or auxiliary agent 21 and/or dissolves the first active substance and/or auxiliary agent. When first elastomer plug 15 is further displaced in the distal direction, an injection can be carried out.

Alternatively, it is possible that primary packaging 1 is configured as a single chamber cartridge, as a single chamber syringe or as a dual chamber syringe. Particularly preferably, primary packaging 1 is configured for ophthalmic applications, the primary packaging in particular including active substances and/or auxiliary agents 21, 23, which are configured for the treatment of eye diseases, in particular macular degeneration, very particularly age-related, diabetes-induced or wet macular degeneration. In this instance, primary packaging 1 is particularly configured to carry out an injection directly into the vitreous body of the human eye, for the purposes of which an outer sterility of primary packaging 1 has to be mandatorily ensured.

Furthermore, primary packaging 1 is preferably configured to administer smaller fill volumes of preferably less than or at most 200 µl, and in particular no more than 50 µl are to be injected into the vitreous body of the human eye. It is possible that primary packaging 1 has a nominal volume of 1 ml or 0.5 ml.

In summary, it is evident that primary packaging 1 provides a primary packaging, which does not have the disadvantages existing in connection with primary packagings made from glass, bearing the risk of detaching, microscopic glass particles and of an intolerable quantity of subvisual particles in one of the active substances and/or auxiliary agents present in primary packaging 1, the packaging means in the filled state simultaneously being terminally sterilizable with the aid of chemical sterilization.

What is claimed is:

1. A primary packaging for medical preparation, comprising:
   a base body constructed of a plastic material, the base body having at least one wall including an outer surface and at least one inner surface, the outer surface provided with a gas tight coating,
   wherein the at least one inner surface is provided with a gas tight inner coating, and an inner functional layer is situated at least in sections on the gas tight inner coating, the inner functional layer is omitted in at least one free region of the at least one inner surface,
   wherein the free region is located in a region of the base body that is configured to receive a freeze drying product solution, a freeze drying material, a lyophilisate, or a combination thereof, and
   wherein the primary packaging is configured as a dual chamber system with a first distal chamber and a second proximal chamber, the first and second chambers being separated by a center plug, wherein the at least one free region is located within the first distal chamber.

2. The primary packaging of claim 1, wherein the gas tight coating has a layer, selected from a group consisting of a metal-including layer, a metalloid-including layer, a silicon-including layer and a silicon compound-including layer.

3. The primary packaging of claim 1, wherein the gas tight coating has a layer including a silicon or silicon composition with a composition selected from a vitreous composition and a quartz-like composition.

4. The primary packaging of claim 1, wherein the plastic material of the base body comprises a transparent plastic material or is made up of a transparent plastic material, wherein the transparent plastic material is selected from a group consisting of a cyclic olefin polymer, a cyclic olefin copolymer and polycarbonate.

5. The primary packaging of claim 1, further comprising an adhesive agent layer situated between the outer surface and the gas tight coating.

6. The primary packaging of claim 1, wherein the inner functional layer comprises hydrophobic or hydrophilic properties.

7. The primary packaging of claim 1, wherein the dual chamber system is selected from a group consisting of a dual chamber cartridge, a dual chamber cartridge and a dual chamber syringe.

8. The primary packaging of claim 1, wherein the primary packaging is configured for an ophthalmic application.

9. The primary packaging of claim 1, wherein the inner functional layer comprises a hydrophobic material selected from the group consisting of polydimethylsiloxane, polytetrafluoroethylene, and combinations thereof.

10. The primary packaging of claim 1, wherein the inner functional layer comprises a hydrophilic material.

11. The primary packaging of claim 10, wherein the hydrophilic material is a plasma-induced polymerization product of acrylic acid.

12. The primary packaging of claim 1, wherein at least one of the gas tight coating of the outer surface or the gas tight inner coating comprises gold, aluminum, chromium, or silver.

13. A primary packaging for medical preparation, comprising:
 a base body constructed of a plastic material, the base body having a wall including an outer surface and an inner surface, the outer surface provided with a gas tight coating, and
 an elastomeric plug disposed within the base body and defining a distal chamber and a proximal chamber, the distal chamber and the proximal chamber being separated by the elastomeric plug,
 a gas tight inner coating disposed on the inner surface, and
 an inner functional layer situated at least in sections on the gas tight inner coating, the inner functional layer being omitted in at least one free region of the inner surface in the distal chamber, wherein the inner functional layer is configured to reduce a sticking friction on the elastomeric plug.

14. The primary packaging of claim 13, further comprising a second elastomeric plug disposed within the base body, wherein the elastomeric plug and the second elastomeric plug are not in direct contact.

* * * * *